(12) United States Patent
Yang

(10) Patent No.: US 10,744,027 B2
(45) Date of Patent: Aug. 18, 2020

(54) THUMB-SUCKING DETERRENT DEVICE

(71) Applicant: Su Jung Yang, Seoul (KR)

(72) Inventor: Su Jung Yang, Seoul (KR)

( * ) Notice: Subject to any disclaimer, the term of this patent is extended or adjusted under 35 U.S.C. 154(b) by 488 days.

(21) Appl. No.: 15/125,742

(22) PCT Filed: Mar. 29, 2015

(86) PCT No.: PCT/KR2015/003054
§ 371 (c)(1),
(2) Date: Sep. 13, 2016

(87) PCT Pub. No.: WO2015/152574
PCT Pub. Date: Oct. 8, 2015

(65) Prior Publication Data
US 2017/0020714 A1    Jan. 26, 2017

(30) Foreign Application Priority Data

Apr. 1, 2014   (KR) .......................... 10-2014-0038925

(51) Int. Cl.
*A61F 5/00* (2006.01)
*A61F 5/50* (2006.01)

(52) U.S. Cl.
CPC ...................................... *A61F 5/50* (2013.01)

(58) Field of Classification Search
CPC .... A61F 5/50; A61F 5/566; A61F 5/58; A61F 13/104; A61F 13/105; A61J 17/001; A61J 17/008; A61J 17/02; A61B 42/10
USPC ....................................................... 128/880
See application file for complete search history.

(56) References Cited

U.S. PATENT DOCUMENTS

| | | | | |
|---|---|---|---|---|
| 969,942 A | * | 9/1910 | Crandall | A61F 5/50 128/880 |
| 2,084,183 A | * | 6/1937 | Blendinger | A61F 5/50 128/879 |
| 2,225,896 A | | 12/1940 | Belknap | |
| 2,564,183 A | * | 8/1951 | Henderson | A61F 13/105 604/304 |
| 4,396,014 A | * | 8/1983 | Pace | A61F 5/50 128/880 |
| 4,506,663 A | * | 3/1985 | Baron | A61F 5/50 128/880 |
| 5,336,555 A | * | 8/1994 | Darras | A61B 42/10 2/159 |

(Continued)

FOREIGN PATENT DOCUMENTS

CN      2256718 Y     6/1997
CN    201617216 U    11/2010
(Continued)

OTHER PUBLICATIONS

International Search Report dated May 21, 2015 in corresponding Application No. PCT/KR2015/003054; 2 pgs.
(Continued)

*Primary Examiner* — Keri J Nelson
*Assistant Examiner* — Adam Baker
(74) *Attorney, Agent, or Firm* — Maier & Maier, PLLC

(57) ABSTRACT

Provided is a thumb-sucking deterrent device including: a finger insertion part and a coupling part disposed on an end of the finger insertion part. The finger insertion part includes an inner sheet, an outer sheet, and a waterproof sheet interposed between the inner sheet and the outer sheet.

8 Claims, 5 Drawing Sheets

(56) References Cited

U.S. PATENT DOCUMENTS

| | | | | |
|---|---|---|---|---|
| 5,797,405 | A | * | 8/1998 | Brock .................... A61F 5/50 128/878 |
| 7,249,385 | B2 | * | 7/2007 | Schukraft ............. A61F 13/068 128/880 |
| 2004/0162512 | A1 | * | 8/2004 | Liedtke ............... A61F 13/0203 602/59 |
| 2006/0219251 | A1 | | 10/2006 | Ray |
| 2013/0104286 | A1 | | 5/2013 | Shawver et al. |

FOREIGN PATENT DOCUMENTS

| | | | |
|---|---|---|---|
| CN | 201860822 | U | 6/2011 |
| GB | 265598 | | 2/1927 |
| JP | 05-068510 | U | 9/1993 |
| JP | H09-210009 | A | 1/1997 |
| JP | 4488410 | B2 | 6/2010 |
| KR | 2001-0079392 | A | 8/2001 |
| KR | 200251593 | Y1 | 11/2001 |
| KR | 2020130000969 | A | 2/2013 |

OTHER PUBLICATIONS

Chinese Office Action dated Apr. 6, 2017, in connection with corresponding CN Application No. 201580016714.4 (8 pgs.).

Japanese Office Action dated Aug. 1, 2017, in connection with corresponding JP Application No. 2017-503752 (5 pgs.).

European Office Action dated Sep. 21, 2017, in connection with corresponding EP Application No. 15 772 840.3 (4 pgs.).

Korean Notice of Allowance dated Nov. 7, 2016, in connection with corresponding KR Application No. 10-2015-0080262 (2 pgs.).

Extended European Search Report dated Jan. 2, 2017, including the Supplementary European Search Report and the European Search Opinion, in connection with corresponding EP Application No. 15772840.3 (6 pgs.).

Chinese Office Action dated Nov. 16, 2017, in connection with corresponding CN Application No. 201580016714.4 (5 pgs.).

Office Action dated Mar. 2, 2020, in corresponding European Application No. 15772840.3; 4 pages.

* cited by examiner

THUMB-SUCKING DETERRENT DEVICE

TECHNICAL FIELD

The present invention relates to a thumb-sucking deterrent device that is easy to be worn and also is capable of reducing the frequency of a thumb-sucking behavior of the infant and minimizing side effects due to festering of the finger when being used for a long time in the case where the thumb-sucking deterrent device is worn to cover the finger of the infant.

BACKGROUND ART

Although thumb-sucking behaviors of infants are caused by an instinctive behavior or an emotional factor, if such behaviors persist for a long time, side effects such as dental anomalies like an openbite and a malocclusion in upper and lower teeth, teeth development disorder, a finger inflammation, and a risk of infection due to an insertion of a contaminated finger into an oral cavity may occur. Furthermore, psychological side effects such as psychological instabilities and habits may occur.

Although various methods such as being scolded from parents, applying a bitter medicine, and attaching a band-aid are used in the past so as to prevent the thumb-sucking behaviors of the infants, since the methods forcibly suppress only thumb-sucking desire of the infants and thus are psychologically undesirable, the methods may not be fundamental solutions.

Also, in recent years, although there has been an attempt to wear a separate deterrent device on the fingers of the infants so as to reduce or eliminate a frequency of the thumb-sucking behaviors of the infants, such a deterrent device according to the related art may have side effects in excessively restricting movement of the finger or festering a portion of the finger, on which the finger and the deterrent device are in contact to each other, due to insufficient ventilation. Thus, such a deterrent device may have some limitations in which the treatment time is hard to be expected, and the therapeutic effect is also low.

Therefore, a thumb-sucking deterrent device is required to be developed, which is capable of reducing a frequency of the thumb-sucking behaviors of the infants without restricting free movement of the finger of the infant, giving superior air-permeability, and preventing saliva of the oral cavity from contacting the finger so that the finger does not fester in spite of wearing the thumb-sucking deterrent device for a long time.

DISCLOSURE OF THE INVENTION

Technical Problem

To solve the foregoing problems of the thumb-sucking deterrent device according to the related art, the present invention is to provides a thumb-sucking deterrent device that reduces a frequency of a thumb-sucking behavior of an infant, has superior air-permeability and absorptivity to improve wearing sensation at a contact portion between the finger and the deterrent device and also prevent festering or scar in the finger from occurring. Furthermore, the present invention is to provide a thumb-sucking deterrent device capable of blocking transfer of saliva in the oral cavity to the finger although the infant suctions the deterrent device. Also, the present invention is to provide a thumb-sucking deterrent device of which a shape is not easily deformable in spite of being sterilized several times in boiling water.

Technical Solution

To solve the above-described problems, the present invention provides a thumb-sucking deterrent device including a finger insertion part which includes an inner sheet, an outer sheet, and a waterproof sheet interposed between the inner sheet and the outer sheet.

Advantageous Effects

According to the present invention, the finger insertion part may be constituted by the three sheets to prevent the waterproof sheet from directly contacting the mouth when the infant suctions the finger on which the deterrent device according to the present invention is worn. Also, the air may flow to the mouth through the outer sheet to reduce the thumb-sucking behavior of the infant. Also, the deterrent device according to the present invention may be inserted on the finger of the infant to give the sense of difference to the finger and to make the visual stimulus, thereby reducing the frequency of the thumb-sucking behavior of the infant.

Also, according to the present invention, the contact portion of the finger insertion part, which directly contacts the finger may be formed of the material having both air-permeability and water-permeability to improve the wearing sensation and also to prevent the festering an the scar of the finger from occurring by easily suctioning the sweat discharged from the finger and the saliva in the oral cavity. Thus, the side effects to the finger of the infant may be minimized in spite of being worn for the long time.

Furthermore, although the infant suctions the finger insertion part, the saliva may not be transferred to the finger to give the comfortable wearing sensation on wearing the deterrent device and to fundamentally prevent the finger from being blistered or festering by the moisture.

MODE FOR CARRYING OUT THE INVENTION

Hereinafter, the present invention will be described in more detail with reference to the accompanying drawings.

Terms or words used in the specification and claims should not be interpreted as being limited to a conventional or dictionary meaning, and should be interpreted as the meaning and concept that accord with the technical spirit on the grounds of the principle that the inventor can appropriately define the concept of the term in order to explain invention in the best way.

Figure 1:
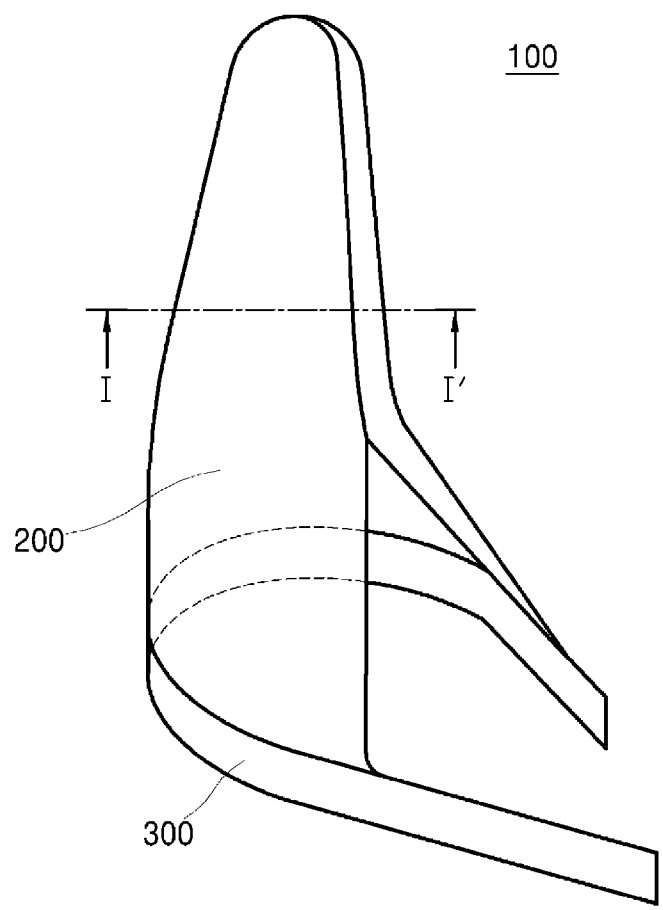
FIG. 1 is a perspective view of a thumb-sucking deterrent device according to an embodiment of the present invention.

FIG. 1 is a perspective view of a thumb-sucking deterrent device according to an embodiment of the present invention. Referring to FIG. 1, a thumb-sucking deterrent device 100 may include a finger insertion part 200. The finger insertion part surrounds a finger of an infant by inserting the finger of the infant into the finger insertion part. For reference, the finger of the infant is not limited to a thumb. When the infant habitually suctions a finger, for example, an index finger, the deterrent device may be worn to the index finger.

The thumb-sucking deterrent device 100 may include the finger insertion part and various fixing units for fixing the finger of the infant to the finger insertion part. For example, the thumb-sucking deterrent device 100 according to an embodiment of the present invention may include a coupling part 300 disposed on an end of the finger insertion part 200.

Also, a cutoff part, which is cut by a predetermined distance from an opening of the finger insertion part 200 in a finger insertion direction, may be provided in a portion of an outer circumference surface of the finger insertion part 200 so that the finger of the infant is easily inserted.

Furthermore, the finger insertion part 200 may include an inner sheet, an outer sheet, and a waterproof sheet interposed between the inner sheet and the outer sheet. Particularly, referring to FIG. 2 that illustrates a cross-sectional view taken along the line I-I' of FIG. 1, the finger insertion part 200 may have at least thee-layered lamination structure including an inner sheet 210 directly contacting the finger of the infant, an outer sheet 230 contacting an oral cavity of the infant, and a waterproof sheet 220 interposed between the inner sheet and the outer sheet.

Each of the inner sheet 210 and the outer sheet 230 may include a material having both air-permeability and absorptivity. For example, each of the inner sheet 210 and the outer sheet 230 may independently include at least one kind or more of materials selected from the group consisting of pulp fiber, cotton fiber, linen fiber, ramie fiber, hemp fiber, fibroin fiber, rayon fiber, polyester/polyethylene-based synthetic fiber, and a superabsorbent polymer of an acrylic acid copolymer. Also, since each of the inner sheet 210 and the outer sheet 230 is formed of a soft material, wearing sensation may increase when the finger insertion part contacts the finger of the infant, and free movement of the finger may not be interrupted. Particularly, since the outer sheet 230 directly contacts a mouth of the infant, it is preferable to use natural materials that are harmless to the infant.

If the inner sheet 210 is formed of a material that does not have the air permeability and the absorptivity, for example, a material such as silicone or latex, since air does not flow through a contact portion between the finger and the deterrent device, a skin of the finger may be adversely influenced when being worn for a long time. Particularly, when sweat is not excreted from the contact portion to remain in the contact portion, the skin is blistered or easily festers. Thus, in the thumb-sucking deterrent device 100 according to an embodiment of the present invention, a portion of the thumb-sucking deterrent device 100, which directly contacts human bodies such as the finger and the oral cavity is formed of a material having the air permeability and the absorbency to give a smooth air flow to the finger skin, thereby providing comfortable environments to the skin. Also, a phenomenon in which the finger is festered may be significantly reduced by absorbing easily the sweat and the saliva.

Each of the inner sheet 210 and the outer sheet 230 may independently have a thickness ranging from 0.1 mm to 5 mm. When each of the inner sheet 210 and the outer sheet 230 has a thickness less than 0.1 mm, a shape maintaining effect and the wearing sensation of the thumb-sucking deterrent device may be deteriorated. Furthermore, an effect of absorbing moisture such as the sweat and the saliva may be slight. Also, when each of the inner sheet 210 and the outer sheet 230 has a thickness greater that 5 mm, the thumb-sucking deterrent device may be disadvantageous in views of a manufacturing process and manufacturing costs.

Also, the waterproof sheet 220 is interposed between the inner sheet 210 and the outer sheet 230 to prevent liquid such as the saliva of the oral cavity from contacting the finger. Thus, it is preferable that the waterproof sheet is formed of a waterproof material that is capable of preventing moisture and the like from passing therethrough. Particularly, the waterproof sheet 220 may include natural rubber latex or at least one kind of more of synthetic resin materials selected from the group consisting of a styrene-ethylene-butylene-styrene copolymer, a styrene-isoprene-styrene copolymer, a styrene-butadiene-styrene copolymer, a styrene-isoprene copolymer, a styrene-butadiene copolymer, synthetic isoprene, polychloroprene rubber, polyvinyl chloride, nitrile rubber, butyl rubber, butadiene rubber, ethylene-propylene rubber, polysulfide-base rubber, silicone rubber, fluorine rubber, or polyurethane.

Since the waterproof sheet 220 has to have no or minimized air permeability and water permeability so as to achieve the foregoing objective of the present invention, it is preferable that the waterproof sheet 220 does not have a pore and the like, through which air is capable of passing. That is, although the saliva and the like is permeated into the outer sheet 230 when the infant suctions the finger insertion part for a long time, the saliva permeated into the outer sheet 230 may not directly reach the finger by the waterproof sheet 220.

Also, if the waterproof sheet 220 has a thickness enough to perform a waterproof function against the saliva and the like, the waterproof sheet 220 may be formed with a thickness relatively less than that of each of the inner sheet 210 and the outer sheet 230. For example, the waterproof sheet 220 may be formed with a thickness ranging from about 0.01 to about 0.5 of the thickness of the inner sheet.

Figure 2:
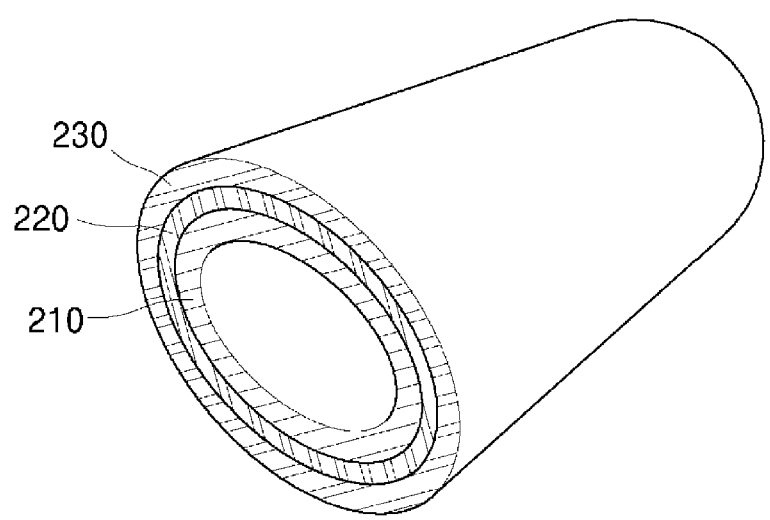
FIG. 2 is a cross-sectional view of a finger insertion part according to an embodiment of the present invention.

According to an embodiment of the present invention, the waterproof sheet 220 may surface-contact the inner sheet 210 and the outer sheet 230 in a non-adhesion manner as illustrated in FIG. 2. That is, the inner sheet 210, the outer sheet 230, and the waterproof sheet 220 may be manufactured in a stacked state without performing a separating adhesion process. In this case, since the waterproof sheet 220 has a thickness relatively less than that of each of the inner sheet 210 and the outer sheet 230, the waterproof sheet 220 may be fixed in position between the inner sheet 210 and the outer sheet 230 in a state of maintaining the shape of the finger insertion part. In addition, since the inner sheet 210 and the waterproof sheet 220, and the outer sheet 230 and the waterproof sheet 220 are fixed in position in the non-adhesion manner, the air may smoothly pass between the inner sheet 210 and the waterproof sheet 220, and thus, the air may be delivered to the contact portion between the skin of the finger and the deterrent device to improve the wearing sensation and the like.

Also, since the waterproof sheet 220 is interposed between the inner sheet 210 and the outer sheet 230, the waterproof sheet 220 may be prevented from being separated to the outside of the inner sheet 210 and the outer sheet 230 in spite of being sterilized several times in boiling water.

Figure 3:
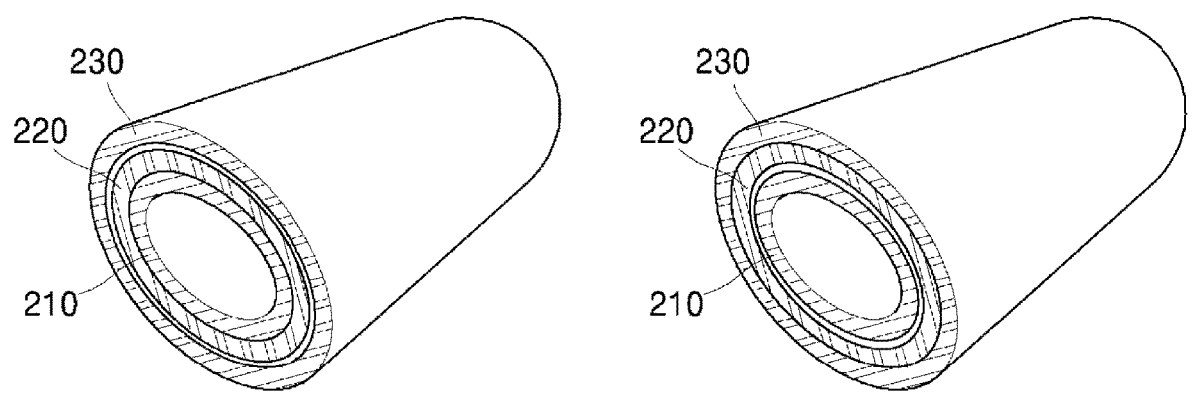
FIG. 3 is a cross-sectional view of the finger insertion part in which a waterproof sheet is laminated on an inner sheet or an outer sheet according to an embodiment of the present invention.

Alternatively, according to another embodiment of the present invention, as illustrated in FIG. 3, the waterproof sheet 220 may be laminated on one of an inner surface of the outer sheet 230 and an inner surface (a surface facing the outer sheet) of the inner sheet 210. In this case, since it is unnecessary to separately cut the waterproof sheet 220 during the process of manufacturing the deterrent device according to the present invention, the manufacturing process may be simplified and advantageous in views of the position fixing of the waterproof sheet 220 and the waterproofing of the saliva. Here, the waterproof sheet 220 may be laminated on both the inner sheet 210 and the outer sheet 230. In this case, however, the air circulation between the sheets may be impossible, and thus, the elimination performance of the moisture such as the sweat and the saliva from the contact portion between the skin of the finger and the deterrent device may be deteriorated. Thus, even though the waterproof sheet 220 is laminated on the inner sheet 210 or the outer sheet 230, it is necessary to allow the waterproof sheet 220 to contact at least one of the inner sheet 210 or the outer sheet 230 in the non-adhesion manner.

Figure 4:
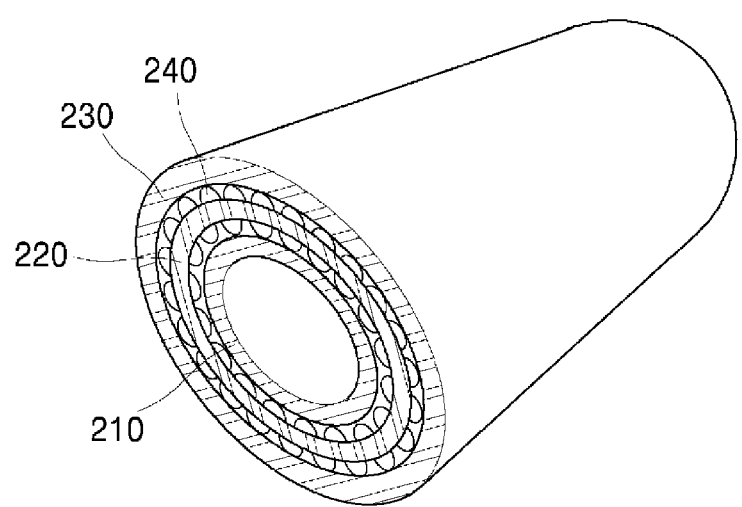
FIG. 4 is a cross-sectional view of a finger insertion part on which embossments are disposed on both surfaces of the waterproof sheet according to an embodiment of the present invention.
Figure 5:
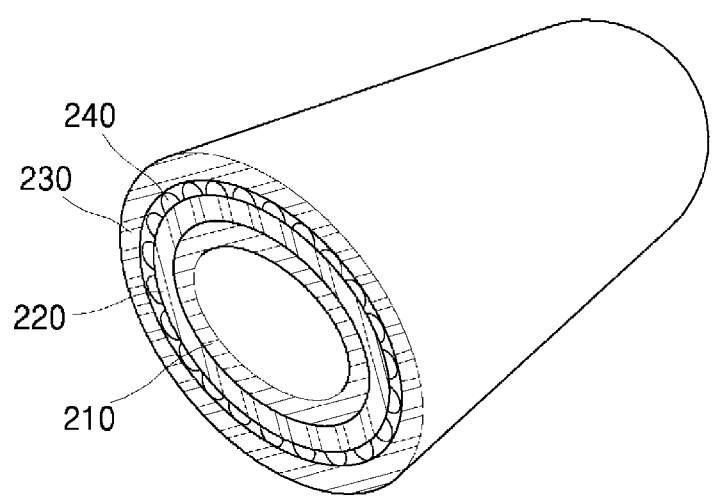
FIG. 5 is a cross-sectional view of a finger insertion part on which embossments are disposed on one surface of the waterproof sheet according to an embodiment of the present invention.

Alternatively, a waterproof sheet 220 according to an embodiment of the present invention may have a plurality of embossments 240 on a surface of the waterproof sheet 220 as illustrated in FIGS. 4 and 5. Particularly, referring to FIG. 4, when the waterproof sheet 220 surface-contacts the inner sheet 210 and the outer sheet 230 in the non-adhesion manner, the embossments 240 may be formed on both surfaces or one surface of the waterproof sheet 220. Also, referring to FIG. 5, when the waterproof sheet 220 is laminated on one of the inner sheet 210 or the outer sheet 230, the embossments 240 may be formed on a surface of the waterproof sheet 220, which is not laminated.

Each of the embossments is not limited in material. For example, the embossment may be formed of the same material as the waterproof sheet 220. An appropriately spaced distance between the waterproof sheet 220 and the inner/outer sheets may be secured by the embossments to secure a passage through which the air smoothly flows.

Also, the thumb-sucking deterrent device may include a coupling part disposed on an end of the finger insertion part. The coupling part prevents the thumb-sucking deterrent device from being separated from the finger of the infant by the movement of the infant's finger or the suction behavior of the infant when the thumb-sucking deterrent device is worn on the finger of the infant. For example, the coupling part may be disposed on the end of the finger insertion part, particularly, a lower end that is adjacent to a wrist or may be formed by using an elastic material that is capable of providing elasticity to the finger insertion part itself.

The coupling part is not limited if the coupling part is a unit capable of providing proper fixing force to prevent the finger insertion part from being separated from the finger. For example, the thumb-sucking deterrent device according to an embodiment of the present invention may include a coupling unit such as a snap fastener on a lower end thereof.

Furthermore, according to an embodiment of the present invention, the coupling part may further include a length-adjustable unit for more firmly wearing the thumb-sucking deterrent device. The length-adjustable unit may be a multistage length-adjustable unit or a contraction-type length-adjustable unit including an elastic band. The length-adjustable unit may be disposed on the lower end of the coupling part, for example, the thumb insertion part.

According to an embodiment of the present invention, the outer sheet may further include various functional components on an outer surface of the outer sheet or within the outer sheet. For example, antimicrobial for inhibiting propagation of microbes that are harmful to the infant or some bitter tasting ingredient for correcting the thumb-sucking behavior of the infants may be further provided.

In addition, a variety of visual effects such as various colors or patterns may be given on the outer sheet 230 to suppress the thumb-sucking behavior of the infant.

The invention claimed is:

1. A thumb-sucking deterrent device comprising:
a finger insertion part,
wherein the finger insertion part comprises an inner sheet, an outer sheet, and a waterproof sheet interposed between the inner sheet and the outer sheet,
wherein each of the inner sheet and the outer sheet has a thickness ranging from 0.1 mm to 5 mm,
wherein the finger insertion part further comprises a distal closed end and a proximal open end,
wherein each of the inner sheet and the outer sheet is formed of a material having air-permeability, and
wherein the inner sheet, the outer sheet, and the waterproof sheet is formed on the distal closed end,
wherein the inner sheet, the outer sheet, and the waterproof sheet surfaces contact each other in a non-adhesion manner and are stacked on each other,
wherein the waterproof sheet has a plurality of embossments on both surfaces or one surface facing the outer sheet so that air flows among the inner sheet, the outer sheet and the waterproof sheet via the plurality of embossments.

2. The thumb-sucking deterrent device of claim 1, wherein each of the inner sheet and the outer sheet independently comprises at least one kind of more of materials selected from the group consisting of pulp fiber, cotton fiber, linen fiber, ramie fiber, hemp fiber, fibroin fiber, rayon fiber, polyester/polyethylene-based synthetic fiber, and a superabsorbent polymer of an acrylic acid copolymer.

3. The thumb-sucking deterrent device of claim 1, wherein the waterproof comprise natural rubber latex or at least one kind of more of synthetic resin materials selected from the group consisting of a styrene-ethylene-butylene-styrene copolymer, a styrene-isoprene-styrene copolymer, a styrene-butadiene-styrene copolymer, a styrene-isoprene copolymer, a styrene-butadiene copolymer, synthetic isoprene, polychloroprene rubber, polyvinyl chloride, nitrile rubber, butyl rubber, butadiene rubber, ethylene-propylene rubber, polysulfide-based rubber, silicone rubber, fluorine rubber, and polyurethane.

4. The thumb-sucking deterrent device of claim 1, wherein the waterproof sheet has a thickness ranging from 0.01 times to 0.5 times of the thickness of the inner sheet.

5. The thumb-sucking deterrent device of claim 1, wherein the waterproof sheet is laminated on one of the inner sheet and the outer sheet.

6. The thumb-sucking deterrent device of claim 1, wherein the finger insertion part comprises a cutoff part defined by cutting a portion of an end of the finger insertion part.

7. The thumb-sucking deterrent device of claim 1, further comprising a coupling part disposed on an end of the finger insertion part.

8. A thumb-sucking deterrent device comprising:
a finger insertion part,
wherein the finger insertion part comprises an inner sheet, an outer sheet, and a waterproof sheet interposed between the inner sheet and the outer sheet,
wherein each of the inner sheet and the outer sheet has a thickness ranging from 0.1 mm to 5 mm, wherein the finger insertion part further comprises a distal closed end and a proximal open end, wherein each of the inner sheet and the outer sheet is formed of a material having air-permeability, wherein the inner sheet, the outer sheet, and the waterproof sheet is formed on the distal closed end, wherein the waterproof sheet is laminated on one of the inner sheet and the outer sheet, wherein the waterproof sheet has a plurality of embossments on both surfaces or one surface thereof, which is not laminated on the inner sheet or the outer sheet so that air flows among the inner sheet, the outer sheet and the waterproof sheet via the plurality of embossments.

\* \* \* \* \*